(12) United States Patent
Skelton

(10) Patent No.: US 6,171,254 B1
(45) Date of Patent: Jan. 9, 2001

(54) CONTROL FOR AUTOMATIC BLOOD PRESSURE MONITOR

(75) Inventor: Brian J. Skelton, Lake Zurich, IL (US)

(73) Assignee: Medical Research Laboratories, Inc., Buffalo Grove, IL (US)

( * ) Notice: Under 35 U.S.C. 154(b), the term of this patent shall be extended for 0 days.

(21) Appl. No.: 09/258,980

(22) Filed: Feb. 26, 1999

(51) Int. Cl.[7] .................................................. A61B 5/02
(52) U.S. Cl. ........................ 600/490; 600/485; 600/493
(58) Field of Search .................................. 600/485–500

(56) References Cited

U.S. PATENT DOCUMENTS

| | | | |
|---|---|---|---|
| 3,585,987 | 6/1971 | Svensson | 128/2.05 Q |
| 3,699,945 | 10/1972 | Hanafin | 128/2.05 C |
| 3,744,490 | 7/1973 | Fernandez | 128/2.05 A |
| 4,109,646 | 8/1978 | Keller | 128/2.05 C |
| 4,116,230 | 9/1978 | Gorelick | 128/2.05 M |
| 4,501,280 | 2/1985 | Hood, Jr. | 128/677 |
| 4,572,205 | 2/1986 | Sjönell | 128/686 |
| 4,768,518 | * 9/1988 | Peltonen | 600/490 |
| 4,924,873 | 5/1990 | Sorensen | 128/677 |
| 4,969,466 | 11/1990 | Brooks | 120/681 |
| 5,003,981 | 4/1991 | Kankkunen et al. | 128/677 |
| 5,022,403 | 6/1991 | LaViola | 128/680 |
| 5,060,654 | 10/1991 | Malkamäki et al. | 128/686 |
| 5,069,219 | 12/1991 | Knoblich | 128/679 |
| 5,172,697 | 12/1992 | Koven et al. | 128/679 |
| 5,240,008 | 8/1993 | Newell | 128/685 |
| 5,243,991 | 9/1993 | Marks | 128/686 |
| 5,301,676 | 4/1994 | Rantala et al. | 128/686 |
| 5,447,160 | 9/1995 | Kankkunen et al. | 128/677 |
| 5,746,213 | 5/1998 | Marks | 128/686 |

\* cited by examiner

*Primary Examiner*—Cary O'Connor
*Assistant Examiner*—Ryan Carter
(74) *Attorney, Agent, or Firm*—Fitch, Even, Tabin & Flannery

(57) ABSTRACT

A blood pressure monitoring system for automatic unattended operation uses curve fitting techniques determined during an initial inflation period to determine cuff size. Based upon cuff size, the number of important predetermined operating parameters are determined for use in controlling the remaining blood pressure reading operations. The automatic blood pressure monitor according to the present invention offers a simplified, cost effective construction utilizing a single pump, a single valve and a single valve orifice.

20 Claims, 2 Drawing Sheets

CONTROL FOR AUTOMATIC BLOOD PRESSURE MONITOR

BACKGROUND OF THE INVENTION

1. Field of the Invention

The present invention relates to the real time monitoring of a patient's blood pressure and in particular to the taking of continuous automatic blood pressure readings.

2. Description of the Related Art

In working with a large number of different automatic blood pressure reading systems, it has been recognized that the deployment of the blood pressure cuff must be carefully considered in order to achieve accuracy in the blood pressure readings taken. It has been observed, for example, that the width of the blood pressure cuff (taken in the direction along the length of the patient's arm) must be maintained within certain ranges in order to prevent erroneous blood pressure readings.

Most of the blood pressure cuffs in use today take the form of a double-ended, elongated strip which is wrapped about as patient's limb with ends of the blood pressure cuff partly overlapping. As a minimal requirement, the amount of overlap must be sufficient to allow proper self-attachment of the strip ends so as to free an operator to perform other tasks, such as operating monitoring equipment. Recently, attention has been paid to the amount of overlap of the blood pressure cuff ends, with the appreciation that errors in overwrap, either too large or too small, even if satisfactory to allow blood pressure readings to be taken, result in an unwanted shift of those readings.

In addition to variations encountered in applying a blood pressure cuff to a patient's limb, a variation of blood pressure readings also arises from the fact that, as a practical matter, there are a relatively large number of different size cuffs by manufacturers of blood pressure reading equipment. For example, systems having nine or more differently sized blood pressure cuffs are not uncommon. Cuff sizes typically include a smallest size blood pressure cuff for neonatal patients and a largest blood pressure cuff size for adult thigh readings. Some blood pressure reading equipment requires the user to specify the cuff size by a special purpose input, such as a special, identifying switch or some other predefined selection means. Other systems require that special pneumatic fittings be employed to provide a self-identification of the size of the blood pressure cuff with which the fitting is associated. Accordingly, some type of keying system between the blood pressure cuff and the associated pneumatic circuitry is employed. The complexities in taking blood pressure readings is growing at a time when increasing demands are being made on care givers and other personnel charged with the responsibility of taking blood pressure readings. The need for an improved, automatic blood pressure reading system still exists.

SUMMARY OF THE INVENTION

It is an object of the present invention to provide a system and method for the automatic, continuous reading of blood pressure.

Another object of the present invention is to provide a system and method of the above-described type which are suitable for use with a plurality of differently sized blood pressure cuffs and which automatically adapt for the accurate use of such cuffs.

A further object of the present invention is to provide a system and method for the automatic reading of blood pressure in which blood pressure cuff size is automatically determined at the initial phase of a blood pressure reading, before the actual blood pressure reading commences, allowing for the calculation of several parameters important to the rapid, comfortable and safe reading of a patient's blood pressure.

These and other objects of the present invention are provided in an automatic, non-invasive blood pressure measuring device of the type which detects blood pressure pulses in a patient's appendage, comprising:

a cuff for constricting blood flow in the patient's appendage;

a pump connected to the cuff for inflation thereof in response to a pump control signal;

valve means connected to the cuff for deflation thereof in response to a valve control signal;

a pressure sensing means connected to the cuff to sense pressure in the cuff and to send a pressure signal in response thereto;

microprocessor means connected to said pump, said valve means and said pressure sensing means, including means to observe the initial pressure-time characteristics of said cuff during an observed inflation period in which the pressure of the cuff is increased to a level less than a target pressure needed to take a blood pressure reading; and said microprocessor means including means for determining the cuff size by comparing the initial pressure-time characteristic of said cuff with stored pressure-time characteristics of cuffs of known sizes, and means for determining, in response to said cuff size determination, a cuff inflation rate, a cuff deflation rate and at least one deflation pressure drop step size, said microprocessor means sending control signals to said pump to inflate said cuff to said target pressure according to said cuff inflation rate, and to deflate said cuff at said deflation rate, using said at least one deflation pressure drop step.

DETAILED DESCRIPTION OF THE PREFERRED EMBODIMENTS

Figure 1:
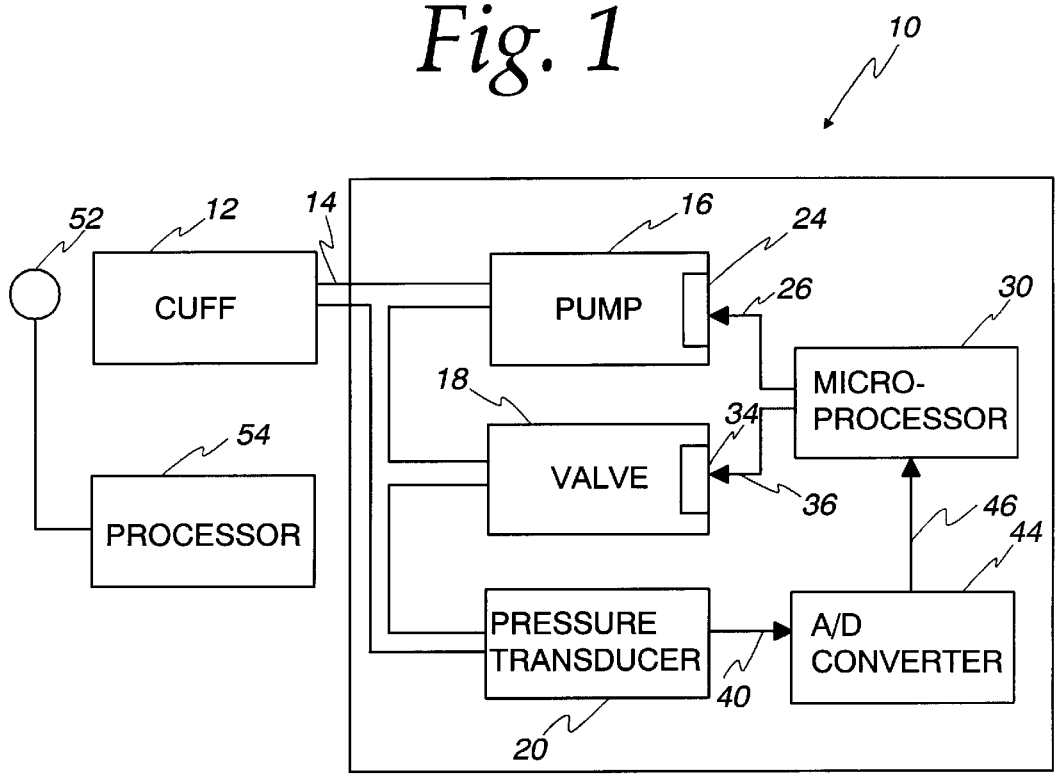
FIG. 1 is a schematic view of an automatic blood pressure monitor according to the principles of the present invention.

Turning now to the drawings, and initially to FIG. 1, the present invention is directed to an automatic blood pressure monitor 10 with automatic cuff size determination and cuff pressure control. A cuff 12 of conventional construction is coupled through a hose, piping or other conduit means to a pneumatic control system, including a pump 16, a valve 18 and a pressure transducer 20. The cuff 12 is wrapped about the patient's arm and operated so as to apply varying amounts of pressure sufficient to selectively occlude and release blood flow through the patient's brachial artery.

Pump 16 is preferably of the positive displacement type operated under control of an electronic system 24. Most preferably, the pump is controlled by duty-cycling the driver circuitry of the pump. The driver portion of system 24 is coupled by control circuit wiring 26 to a microprocessor 30.

Microprocessor 30 is of a conventional type issuing control instructions, e.g., in the form of a pulse train, to the pump driver of system 24. The presence or absence of pulses in the pulse train control the duty cycle of the pump, which in turn directly controls the pump output, i.e., the inflation rate and inflation volume of cuff 12.

The valve 18 is pneumatically coupled to cuff 12 and provides selective venting or deflation of the cuff in a controlled manner, preferably by duty-cycling the driver circuitry 34 of the valve. Valve driver 34 is coupled by control circuitry 36 to microprocessor 30. The valve 18 is preferably of the on/off control type (as opposed to more costly proportional valves). Depending upon the duty cycle control signal transmitted through conductor 36 to valve control circuitry 34, the valve is held closed or open with a number of different deflation rates.

A pressure transducer 20 monitors the pressure of cuff 12 and sends an electrical output signal indicating the pressure, via conductor 40 which couples the pressure transducer 20 to an analog/digital converter 33. The analog/digital converter 44 is in turn coupled to microprocessor 30 by conductor 46. Preferably, the driver circuitry 24 of pump 16 operates under closed loop control implemented by microprocessor 30. Similarly, the valve driver circuitry 34 of valve 18 undergoes closed loop operation under control of microprocessor 30. Although principles of the present invention may be readily employed with pneumatic control systems having multiple pumps, multiple valves and/or multiple orifices, present invention is particularly advantageous in providing heretofore unattainable control with simple, low-cost components, including a single pump, a single valve and a single valve orifice arrangement.

In the preferred embodiment, the monitoring system uses an oscillometric method of determining blood pressure, sensing pulses with pressure transducer 20. If desired, as an alternative, an acoustic, ultrasonic or strain gage transducer 52 could be located in the vicinity of cuff 12 for audibly monitoring blood flow in the brachial artery. The alternative transducer is shown coupled to conventional pulse discriminator circuitry 54 which could also be implemented, for example, in microprocessor 30. Together, the transducer and pulse discriminator circuitry, either standing alone or incorporated in microprocessor 30, detect the presence of blood flow in the patient's appendage, monitor the number of heart-induced pulses in the arterial blood flow and measure the relative amplitudes of those arterial pressure pulses.

Typically, the blood pressure cuff 12 is initially inflated to a suprasystolic pressure level at which blood flow is cut off in the patient's limb, herein the brachial artery. As an alternative to a complete cessation of blood flow in the brachial artery, pressure can be increased in cuff 12 so as to apply sufficient pressure to impede blood flow in the brachial artery to a point where the pulse beat is either substantially reduced or can no longer be detected. Thereafter, pressure applied to the brachial artery by the cuff 12 is reduced by relaxing pressure in cuff 12 in a controlled manner until the first very weak pulse is detected, and this pressure is immediately related to a pressure above the patient's systolic blood pressure level. As the pressure in cuff 12 is reduced, the pressure is continuously detected by transducer 20 and monitored by microprocessor 30.

After the first faint pulses are reliably detected, cuff pressure is reduced by a controlled amount and held at the reduced level for a defined period of time, long enough to acquire additional pulse information. Most preferably, each "pressure hold" step is sustained long enough to reliably detect two adequately discerned blood pressure pulses. Eventually, with a sufficient number of cuff pressure reductions having been carried out, the amplitude of the blood pressure pulses is typically observed to rise to a maximum value and then fall to a point where blood pressure pulses can no longer be detected, an operating point below the patient's diastolic pressure reading. As will be seen herein, the present invention affords a number of significant advantages in obtaining blood pressure readings in as short an operating time as is practical.

Briefly, the present invention operates early on so as to identify as quickly as possible the size of the blood pressure cuff in sufficient time so as to allow calculation of a number of important control parameters and to thereafter control a substantial portion (and preferably the major portion) of the cuff's inflation period (i.e., the time during which the cuff is brought to a carefully defined patient-specific suprasystolic pressure level, which is approximately the maximum pressure experienced by the cuff.

The required sequence of blood pressure readings occurs at points located below suprasystolic pressures, and taken after the inflation period, when the cuff is continuously deflated until a sub-diastolic pressure level is attained. Thereafter, if additional blood pressure pulse information is desired for the same patient (due, for example, to artifacts caused by motion), pressure may be increased to a controlled supradiastolic level. If a complete repetition of the blood pressure analysis is desired, pressure is elevated once more to a suprasystolic pressure level to enable a repeated observation of the patient.

It is important that cuff 12 be inflated as quickly as possible so as to allow the actual blood pressure measurements to be taken as quickly as possible. However, it has been found that patients react with alarm to high inflation rates, particularly those carried out under automatic control of an unattended machine. This could result in alterations of a patient's vital signs or induce motion artifacts by agitating the patient. The maximum pressure level is particularly important for neonatal and other relatively young patients where a risk of injury may be present if cuff pressures are allowed to assume elevated levels. Control of neonatal blood pressure cuffs has traditionally proven to be unusually difficult because of the smaller volume capacities of the blood pressure cuff used on relatively young patients. The present invention offers improved protection while allowing very rapid determination of blood pressure cuff size, one which can be taken using relatively inexpensive components and in such a rapid manner that pressure levels even for relatively small neonatal cuff sizes are well below acceptable elevated pressure levels.

Once the determination of cuff size has been made, the present invention determines a number of important operating parameters, including the "rate" of inflation over the inflation rate period (preferably the $\Delta p$ and $\Delta t$ values from beginning to end of the inflation rate period), the target pressure, the rate of deflation needed to secure data about the systolic and diastolic blood pressure levels, and the overshoot control employed in step-wise deflation, i.e., pressure reduction, over the time period that blood pressure readings are taken.

Figure 2:
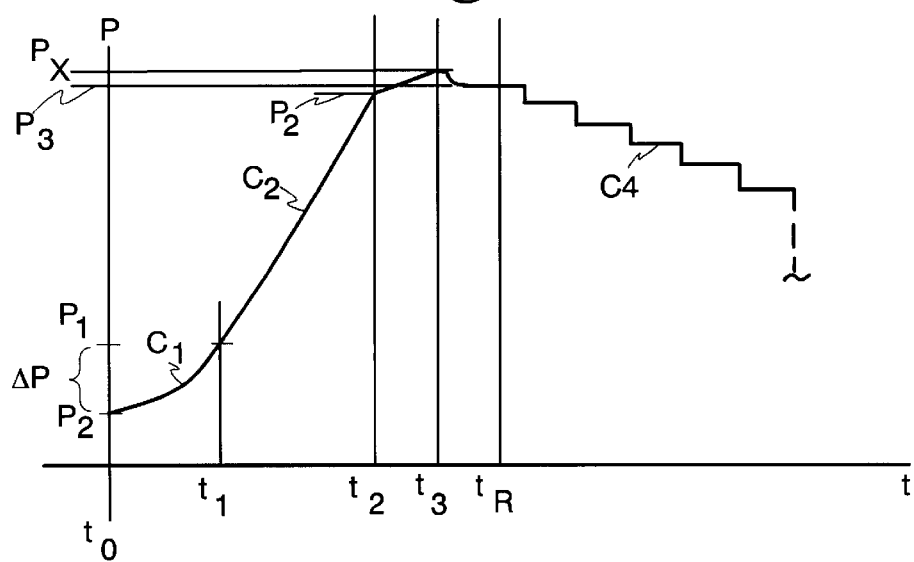
FIG. 2 shows an inflation profile with operation according to principles of the present invention.
Figure 3:
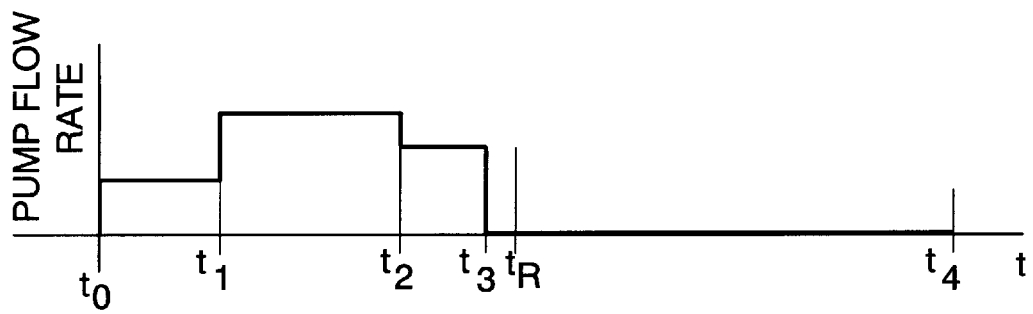
FIG. 3 is a graph showing the pump flow rate associated with the operating curve of FIG. 2.

Turning now to FIGS. 1–3, operation of the blood pressure monitor begins with cuff 12 substantially deflated, indicated by pressure $P_0$ in FIG. 2. As will be seen herein, the blood pressure reading cycle is begun later, approximately at time $t_R$ after an elevated, substantially maximum target pressure $P_3$ is reached. As indicated by the operating curve in FIG. 2, the pressure in the cuff must be substantially increased beyond the initial pressure $P_0$ and a substantial amount of time indicated by the interval between $t_0$ and $t_3$ is needed to fully inflate the cuff. During the time required to inflate cuff 12, a brief initial inflation period ($t_0$ to $t_1$ is defined, and data characteristic of the cuff is accumulated and analyzed. Based upon the results, several important factors are calculated at time $t_1$, in time to set pump 16 and valve 18 for the remainder of the operation.

As a first step, between time $t_0$ and $t_1$, herein the initial inflation period, cuff 12 is inflated to a relatively low pressure level, preferably a small fraction of the operating pressure $P_3$. As graphically indicated in FIG. 2, this portion of the operating curve designated $C_1$ is non-linear and, the curve shape has been found to be characteristic of the size of the cuff being inflated. During the initial inflation period, the cuff may be inflated in a number of different ways. However, the cuff is preferably inflated with a constant flow rate for a pre-defined period of time. That is, the time interval of the initial inflation from $t_0$ to $t_1$ is preferably fixed as part of the program control loaded into microprocessor 30. In the preferred embodiment, the initial inflation period is set so as to assure that, for the smallest blood pressure cuff possible (usually neonatal size) the final pressure at a constant flow rate is well below the appropriate patient-specific maximum operating pressure (i.e., approximately $P_3$ in FIG. 2). At the end of the initial inflation period, pressure is elevated to level $P_1$ and the time interval has allowed a pressure difference of $P_1-P_0$, herein $\Delta P$. It is preferred that the characteristic shape of the initial inflation curve $C_1$ is calculated or otherwise determined immediately at time $t_1$ by microprocessor 30, based upon readings of pressures sensed by transducer 20 and converted into digital form by converter 44.

Referring to FIG. 3, the initial rate of flow is constant throughout the initial inflation period. In order to obtain as rapid a processing time as possible, the rate of flow changes indicated by FIG. 3 are carried out in a step-wise manner, although sloped or curved flow rate changes may also be employed.

Figure 4:
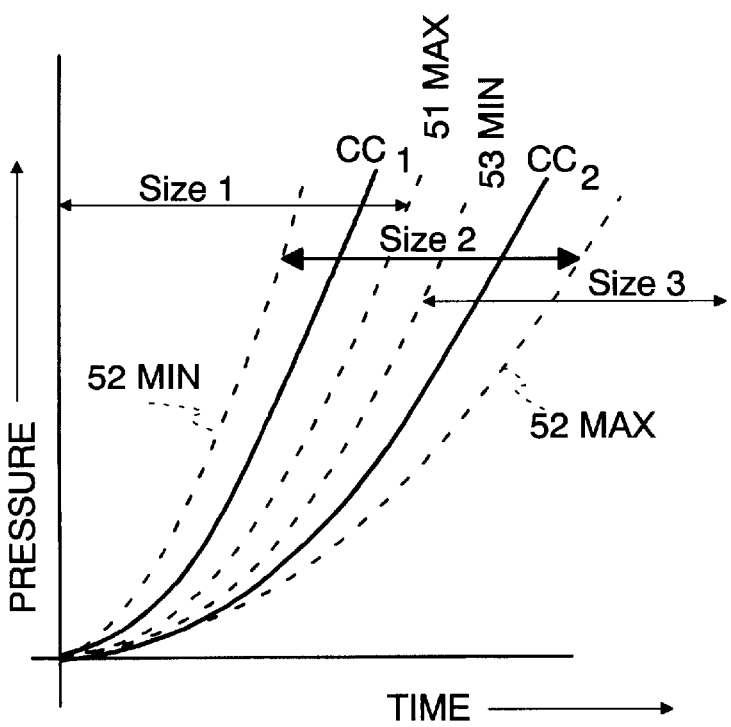
FIG. 4 shows an initial portion of the operating curve, taken on an enlarged scale.

Referring briefly to FIG. 4, a family of characteristic curves for three different blood pressure cuff sizes is shown. For example, for a "size 1" cuff, the smallest cuff size shown, the inflation curves lie between the ordinate and curve $S1_{max}$. The characteristic curves for the next largest cuff size lie between boundaries $S2_{min}$ and $S2_{max}$. The next largest cuff size is associated with an operating region beginning with boundary $S3_{min}$ and extending to the right, beyond the area shown in FIG. 4.

As mentioned, a relatively large number of cuff sizes is found in modern commercial blood pressure reading systems. For the system shown in the preferred embodiment, nine different cuff sizes are assumed. FIG. 4 depicts characteristic operating curves for the three smallest cuff sizes. It has been found that, due to manufacturing tolerances as well as variations in the conformance of the materials employed, a single well-defined characteristic curve is not observed for practical blood pressure cuffs. Rather, as is indicated in FIG. 4, the characteristic curve for a plurality of the same size blood pressure cuffs falls within a range, lying between minimum and maximum limits.

Although more precise recognition schemes can be employed, it has been found expedient for rapid, real time control to pre-define characteristic curves $CC_1$ and $CC_2$ as shown in FIG. 4 lying within the overlap regions and most preferably at the maximum observed limits for each particular size. As can be seen in FIG. 4, the first characteristic curve $CC_1$ is located slightly to the left of $S1_{max}$, between $S2_{min}$ and $S1_{max}$. Similarly, characteristic curve $CC_2$ is located slightly to the left of curve $S2_{max}$, lying between curves $S3_{min}$ and $S2_{max}$. For the purpose of determining control parameters, it should be understood that other curves can be employed which are not related to a specific cuff size. For example, the number of characteristic curves for the family of adult size cuffs can be reduced in number, since it has been found that certain control parameters for certain grouped cuff sizes (neonatal, infant, adult) can be shared for several different cuff sizes within the same group.

For nine different cuff sizes in the blood pressure monitor of interest, nine characteristic curves will be predetermined and stored in microprocessor 30. As cuff pressure data is taken in the initial inflation period $t_0$ to $t_1$, curve data represented as a solid continuous curve portion $C_1$ is accumulated in microprocessor 30 and is compared against the pre-defined characteristic curves. The closest curve fit lying immediately to the right of the observed curve portion indicates the determined cuff size. In practice, cuff size determinations can be made very quickly without substantial delay, at time $t_1$. A series of formulas or look-up tables are then employed by microprocessor 30 to determine a number of important operating parameters which control system operation beyond time $t_1$. An example will be given below.

Before proceeding with a further discussion of operating parameters determined by the present invention, it should be understood that relatively inexpensive equipment can be employed to acquire and interpret enough pressure data points between times $t_0$ and $t_1$ to form a substantially solid curved portion as indicated in FIG. 2. It has been found sufficient in practicing the present invention to forego expensive computer control equipment and to rely instead on data collected as a series of spaced apart operating points. In its simplest form, the present invention looks at the pressure difference over the initial inflation period and scans a table of characteristic values to determine blood pressure cuff size. An adjustment must be made, however, for different initial pressure levels $P_0$. Other types of "curve fitting" can be employed using "least squares fit" and other known techniques.

Once the blood pressure cuff size is determined, a number of operating parameters are determined and are loaded by the control program of microprocessor 30. One parameter determined is the inflation rate between time $t_1$ and time $t_2$, represented by the step increase at time $t_1$ in FIG. 3. It is generally preferred that the operating curve portion $C_2$ during this time period be substantially linear in shape, although other shaped inflation curves could be employed as well. Preferably, the slope of curve portion $C_2$ is pre-defined in a look-up table where other data, based upon observed patient response for the particular size blood pressure cuff, is stored.

It is desirable to shorten the inflation time period $t_1-t_2$ as much as possible. However, excessive rates of inflation are known to startle patients if the inflation is perceived as being near instantaneous, or if the rate of rapid constriction of the patient's appendage is perceived as being surprisingly steep. All of these factors tend to alarm certain patients, with expected physiological reactions resulting. Accordingly, the stored inflation rate values for curve portion $C_2$ are a trade-off between speed and unintended patient response. With the present invention, the differing slope values for differing cuff sizes can be tailored for optimal results.

Referring again to FIGS. 2 and 3, another important parameter determined by cuff size is the maximum operating pressure needed for blood pressure readings, identified as pressure $P_3$ in FIG. 2. In an effort to avoid expensive inflation equipment with more elaborate overshoot control, and to allow the use of single hose cuffs, the automatic control provided by the present invention provides an over-shoot control time period $t_2$–$t_3$ during which the rate of inflation is reduced a small amount as indicated by the step drop at time $t_2$ in FIG. 3. As can be seen in FIG. 2, the attendant pressure-time response of the cuff is non-linear but, with prior testing of known cuffs, the time interval of the over-shoot control period can be accurately determined and stored as a control parameter in a cuff-size related look-up table accessible by microprocessor 30. As can be seen in FIG. 2, the pressure reaches an absolute maximum $P_x$ during the over-shoot control period although, with sufficient pas-sage of time the pressure level is stabilized at time $t_3$ in preparation for the beginning of a blood pressure reading cycle.

At time $t_R$ the blood pressure reading cycle is initiated along with deflation of the blood pressure cuff. According to the present invention, it is preferred that deflation during the blood pressure reading, i.e., between times $t_3$ and $t_4$, have a constant rate of pressure change, that is, a linear dP/dt characteristic shape. The pressure level $P_3$ is defined at the beginning of the blood pressure reading cycle and its value is determined based upon the blood pressure cuff size. Preferably, the beginning reading pressure $P_3$ is obtained by consulting a look-up table stored within microprocessor 30. Generally, the pressure level $P_3$, although different for each cuff size or perhaps cuff group (i.e., neonatal, infant, adult), is associated with a suprasystolic level for the appendage involved. As indicated in FIGS. 2 and 3, it is preferred that pressurization of the cuff is terminated at approximately time $t_3$ and thereafter the cuff is deflated by operation of valve 18 under control of microprocessor 30.

As mentioned, at approximately time $t_1$ the observed curve data is compared against stored values to determine the blood pressure cuff size. This result is used to determine a number of important operating parameters and the first parameter needed is the inflation rate or inflation curve shape between times $t_1$–$t_2$. As a practical matter, the initial target pressure $P_3$ is also determined about time $t_1$, along with the deflation rate between times $t_3$ and $t_4$, as well as the individual overshoot controls and valve duty cycles for deflation pressure drops indicated in the stair step curve portion $C_4$. If desired, the determination of the maximum pressure can be delayed until a time shortly prior to $t_2$, the end point of the over-shoot control period $t_3$ can be delayed until a time after $t_2$ and the deflation rate and step size can be delayed until time $t_3$, if desired. However, it has been found expedient to perform all necessary parameter deter-minations approximately at time $t_1$ and this is found to be readily achievable using modestly priced components.

As will be apparent, a wide variety of step configurations can be employed to accommodate the same deflation rate slope. It is preferred in practicing the present invention that the deflation control parameters be pre-defined for each cuff size and stored in memory, available to microprocessor 30. Upon identification of the cuff size, the number of steps defined either by the pressure drop of each step or the time period between steps is then used to control, preferably in a duty-cycle fashion, the driver 34 of valve 18 to achieve the performance desired.

Only a few deflation steps are shown in FIG. 2 for purposes of illustration. It is preferred in practicing the present invention that the time period between adjacent pressure drop steps be chosen to allow for artifact and motion rejection for the data collected in the appendage being monitored. In the example given, the brachial artery is monitored, and the pressure $P_3$ applied to the patient's upper arm is high enough to assure either that blood flow is substantially occluded in the brachial artery or is otherwise reduced as required. Each step during deflation allows for matching arterial pressure pulses based upon pre-determined data for patients monitored by the particular cuff size employed. The blood pressure pulses are preferably moni-tored by the pressure transducer 20, but, as mentioned, may also be monitored by microphone 52 and a conventional audio processor 54, such as one of the Korotkoff pulse determination type, doppler (ultrasonic) or tonometry (strain gage array) techniques.

Over the evaluation period $t_3$–$t_4$, after a certain number of deflation steps are carried out, blood pressure pulses will be detected and the history of the blood pressure pulse data will be stored in micro-processor 30 for future reference.

Throughout the deflation period, the amplitude of the blood pressure pulses will change over time, typically rising to a maximum value at the mean arterial pressure, thereafter falling to a minimum, final value toward the end of the blood pressure reading, at a time before time $t_4$. The number of steps during the deflation period $t_3$–$t_4$ are chosen to allow accurate detection of the systolic, diastolic and MAP values, while assuring that at least two matching pressure pulses are observed for each step interval. If desired, the blood pressure drop at each step can be held constant throughout the deflation period or can be varied throughout the deflation period according to pre-defined values stored in micropro-cessor 30 for the particular blood pressure cuff size. In any event, the ending point $t_4$ of the blood pressure reading cycle is chosen to be substantially beyond the time when the final detectable blood pressure pulse is detected.

It has been found desirable at time $t_4$ to reduce the pressure in the cuff to a value approximately equal to the initial pressure level $P_0$ or below. Given the speed and ease of operation made possible by the present invention, a repeat of the entire operation $t_0$–$t_4$ may be elected in which case the initial inflation of the cuff can be immediately begun for the subsequent operation. A substantially instantaneous pressure drop is indicated at time $t_4$. Typically, final depressurization occurs over time with a sloped or curved operating charac-teristic. In a subsequent immediately consecutive operating sequence, the systolic, MAP and diastolic values that were previously observed can be used to adjust the beginning of the deflation period so as to reduce the overall reading times.

An example of initial parameter determination will now be given.

The following is an example of the cuff detection process according to the present invention, assuming a simplified system having five different cuff sizes. Reference is made to the following table showing pressure-time relationships empirically determined for each particular pneumatic con-trol system of interest. The pressure thresholds in the fol-lowing table are determined from pressure versus time curves for each cuff size. In the following table, three initial pressure ranges and four cuff size thresholds are considered.

Sample Table Of Cuff Determination Pressure Thresholds

| Initial Pressure (mmHg) | Pressure Threshold @ 11 | Pressure Threshold @ 12 | Pressure Threshold @ 13 |
|---|---|---|---|
| 0–4 | 58 | 74 | 80 |
| 4–7 | 80 | 119 | 130 |
| 7–10 | 94 | 132 | 151 |

Cuff Determination Process

1. The valve is open at the beginning of a blood pressure determination cycle and the pressure in the cuff is monitored. If the pressure in the cuff is >10 mmHg, the valve is left open until the pressure drops below 10 mmHg.

2. The initial pressure in the cuff is determined and the pressure thresholds are obtained from the corresponding row of the table above (i.e., if the initial pressure is 0–4 mmHg, the pressure thresholds at 11, 12 and 13 will be 58, 74 and 80 mmHg, respectively.

3. The valve is closed, and the pump is turned on at a fixed slow, flow rate. The cuff pressure/time relationship (dP/dt) is measured and is compared to the threshold for the smallest cuff first and then for increasingly larger cuffs until a cuff size is determined.

4. The pressure in the cuff is monitored for up to 11 seconds while inflating. If the pressure in the cuff exceeds the pressure threshold for 11 (58 mmHg in this example) prior to 11, the smallest cuff size has been detected. The initial target inflation pressure, inflation, parameters, and deflation parameters are then set for this cuff.

5. If the pressure threshold for 11 has not been exceeded, the pressure in the cuff is monitored until either 12 seconds has been reached, or the pressure threshold for 12 has been exceeded. If the pressure threshold for 12 has been exceeded prior to 12, the next larger cuff size has been detected and he parameters are set for this cuff size.

6. If the pressure threshold for 12 has not been exceeded, step 5 is repeated while monitoring for subsequent pressure and time thresholds until a cuff size has been determined.

7. Once a cuff size has been determined, the inflation parameters are set and the cuff is inflated until the initial target inflation pressure has been reached. At this time the blood pressure reading cycle begins and the cuff is deflated using the cuff deflation parameters for the detected cuff size until a blood pressure determination is made.

The following parameter table was developed for the five cuff sizes studied.

Sample Cuff Size Parameter Table

| Cuff Size | Initial Target Inflation Pressure | Inflation Duty Cycle | Inflation Overshoot Parameter | Deflation Duty Cycle | Deflation Overshoot Parameter |
|---|---|---|---|---|---|
| 1 | 100 | 30% | −3 | 30% | +4 |
| 2 | 125 | 40% | −1 | 40% | +1 |
| 3 | 148 | 70% | 0 | 50% | 0 |
| 4 | 170 | 100% | +1 | 70% | 0 |
| 5 | 170 | 100% | +2 | 70% | −1 |

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. An automatic, non-invasive blood pressure measuring device of the type which detects blood pressure pulses in a patient's appendage, comprising:
  a cuff for constricting blood flow in the patient's appendage;
  a pump connected to the cuff for inflation thereof in response to a pump control signal;
  valve means connected to the cuff for deflation thereof in response to a valve control signal;
  a pressure sensing means connected to the cuff to sense pressure in the cuff and to send a pressure signal indicating a pressure-time characteristic of said cuff in response thereto;
  microprocessor means connected to said pump, said valve means and said pressure sensing means, including means to observe the initial pressure-time characteristic of said cuff during an observed inflation period in which the pressure of the cuff is increased to a level less than a target pressure needed to take a blood pressure reading; and
  said microprocessor means including means for determining the cuff size by comparing the initial pressure-time characteristic of said cuff with a set of stored pressure-time characteristics of cuffs of known sizes, and means for determining, in response to said cuff size determination, a cuff inflation rate, a cuff deflation rate and an initial target pressure, said microprocessor means sending control signals to said pump to inflate said cuff to said target pressure according to said cuff inflation rate, and to deflate said cuff at said deflation rate, using said at least one deflation pressure drop step.

2. The device of claim 1 wherein said pressure sensing means is employed to detect the blood pressure pulses in a patient's appendage.

3. The device of claim 1 wherein said microprocessor means sends control signals to said pump to inflate said cuff to approximately said target pressure at a substantially constant flow rate.

4. The device of claim 1 wherein said microprocessor means sends control signals to said pump to deflate said cuff at a substantially constant deflation rate.

5. The device of claim 1 wherein said microprocessor means sends control signals to said pump to reduce the inflation rate immediately before sending control signals to said valve to deflate said cuff.

6. The device of claim 1 wherein said set of stored pressure-time characteristics of cuffs of known sizes comprises a table of a plurality of discrete pressure and time values, said plurality corresponding to the number of cuff sizes.

7. The device of claim 1 wherein, during said observed inflation period, inflation is carried out for a preselected period of time.

8. The device of claim 7 wherein, during said observed inflation period, inflation is carried out at a substantially constant flow rate.

9. The device of claim 1 further comprising an acoustical detection means which is employed to detect the blood pressure pulses in a patient's appendage.

10. A method for the non-invasive automatic measuring of blood pressure of a patient by detecting blood pressure pulses in a patient's appendage, using a blood pressure cuff of unknown size to selectively restrict blood flow in the patient's appendage, comprising the steps of:

provic a pump connected to said cuff for inflation thereof in response to a pump control signal;

providing a valve means connected to said cuff for deflation thereof in response to a valve control signal;

providing pressure sensing means connected to said cuff to sense pressure in said cuff and to send a pressure signal indicating a pressure-time characteristic of said cuff in response thereto;

providing a microprocessor means coupled to said pump, said valve means and said pressure sensing means;

sending a pump control signal to said pump to inflate said cuff during an observation period to a pressure below that required to take a blood pressure reading, and to observe the pressure-time characteristic during said observation period;

comparing the pressure-time characteristic obtained during said observation period to a set of pressure-time characteristics of cuffs of known sizes so as to determine the cuff size employed;

determining, in response to the determination of the cuff size, a target pressure and an inflation rate to inflate the cuff to approximately the target pressure needed to take a blood pressure reading, the deflation rate of the cuff during a blood pressure reading period;

inflating said cuff according to said inflation rate; and deflating said cuff according to said deflation rate.

11. The method of claim 10 wherein blood pressure readings are taken in between said deflation pressure drops.

12. The method of claim 10 wherein at least two blood pressure pulses are observed between consecutive deflation pressure drops.

13. The method of claim 10 wherein said cuff is inflated at a substantially constant inflation rate.

14. The method of claim 10 wherein said cuff is deflated at a substantially constant deflation rate.

15. The method of claim 10 wherein the inflation rate is reduced immediately before deflating said cuff.

16. The method of claim 10 wherein said set of pressure-time characteristics of cuffs of known sizes is stored in a table of a plurality of discrete pressure and time values.

17. The method of claim 10 wherein said observed inflation period is carried out for a preselected period of time.

18. The method of claim 10 wherein said observed inflation period is carried out at a substantially constant flow rate.

19. The method of claim 10 wherein said pressure sensing means is employed to detect the blood pressure pulses in a patient's appendage.

20. The method of claim 10 wherein, in said deflating step, said cuff is deflated using a valve duty cycle determined in response to said cuff size determination.

* * * * *